(12) United States Patent
Haukap

(10) Patent No.: US 9,827,145 B2
(45) Date of Patent: Nov. 28, 2017

(54) EAR AND EYE PROTECTION SYSTEM

(71) Applicant: Wyatt R. Haukap, Carroll, IA (US)

(72) Inventor: Wyatt R. Haukap, Carroll, IA (US)

( * ) Notice: Subject to any disclaimer, the term of this patent is extended or adjusted under 35 U.S.C. 154(b) by 149 days.

(21) Appl. No.: 14/797,220

(22) Filed: Jul. 13, 2015

(65) Prior Publication Data

US 2016/0199228 A1 Jul. 14, 2016

Related U.S. Application Data

(60) Provisional application No. 62/102,195, filed on Jan. 12, 2015.

(51) Int. Cl.
*A61F 9/02* (2006.01)
*A61F 11/14* (2006.01)

(52) U.S. Cl.
CPC .............. *A61F 9/029* (2013.01); *A61F 11/14* (2013.01)

(58) Field of Classification Search
CPC ........... A61F 9/029; A61F 11/14; A61F 11/06
USPC ..... 2/431; 455/350–353, 347; 351/148, 155, 351/159.03; 381/373
See application file for complete search history.

(56) References Cited

U.S. PATENT DOCUMENTS

| | | | | |
|---|---|---|---|---|
| 4,529,057 A | * | 7/1985 | Telford | A61F 11/14 128/868 |
| 4,670,911 A | * | 6/1987 | Dunford | A61F 9/029 2/209 |
| 8,107,663 B2 | * | 1/2012 | Lin | H04R 1/1041 181/133 |
| 2006/0015989 A1 | * | 1/2006 | Faussett | A61F 11/14 2/423 |
| 2011/0209273 A1 | * | 9/2011 | Fountain | A61F 11/14 2/423 |

* cited by examiner

*Primary Examiner* — Khaled Annis
*Assistant Examiner* — Timothy K Trieu
(74) *Attorney, Agent, or Firm* — Christopher A. Proskey; BrownWinick Law Firm

(57) ABSTRACT

An eye and ear protection system includes a pair of ear muffs connected together by a strap, the ear muffs include a slot in their forward side that is connected to a cavity within the ear muffs. The arms of a pair of glasses are positionable within the slots and allow a user to move the glasses between an in the line-of-sight position and an out of the line-of-sight position. The ear muffs also include one or two doors that can be opened, to allow the user to hear sounds in the environment, and closed to protect the user from loud noises in the environment. This system improves comfort and allows the user to selectively deploy hearing protection and/or eye protection without the need to remove the system from their head which saves time and reduces the potential for losing or misplacing either the hearing or eye protection.

20 Claims, 7 Drawing Sheets

EAR AND EYE PROTECTION SYSTEM

CROSS REFERENCE TO RELATED APPLICATION

This application claims the benefit of U.S. Provisional Application No. 62/102,195 filed Jan. 12, 2015.

FIELD OF THE INVENTION

This invention relates to personal safety equipment. More specifically, and without limitation, this invention relates to a combination hearing protection system and eye protection system.

BACKGROUND OF THE INVENTION

Hearing protection as well as eye protection are incredibly important considerations for anyone that works with equipment or machinery where loud noises are generated and the possibility exists for particles or objects to get into their eyes. This is especially true for persons involved in the trades, farmers, construction workers, machinists, landscapers, mechanics, hobbyists, maintenance workers, or any other person who works with tools, machinery or equipment.

Various hearing protection systems and eye protection systems have been developed, however each suffer from their own disadvantages.

As one example, various ear plugs or ear plug systems have been developed that protect one's hearing. Generally, these ear plug systems include a soft and flexible member that is compressed and then inserted into the ear canal. Once inserted, the flexible material expands and seals to the ear canal. While ear plug systems can easily be used with safety glasses, because they do not interfere with the area around the ear, they have their deficiencies. Namely, ear plugs are time consuming to insert, they can be difficult to remove, they can be easily lost or misplaced because of their small size, they can easily get dirty or soiled, their efficacy varies greatly based on a number of factors, they are incompatible with many person's ears and they can be uncomfortable to wear, among countless other disadvantages.

As another example, as an alternative to using ear plugs, ear muff systems were designed. Generally, ear muff systems include a pair of ear muffs that cover the user's ear and are connected by a strap that goes over the user's head. While ear muff systems can effectively protect a user's hearing, because the ear muffs cover the user's ear, as well as the area around their ear, ear muffs are difficult or impossible to use with safety glasses. When attempting to use ear muffs and safety glasses, the user must choose between two unappealing options, placing the arms of the safety glasses above the ear muffs, or placing the arms of the safety glasses under the ear muffs. It is undesirable for the user to place the arms of safety glasses above the ear muffs because: this tends to place the safety glasses at an awkward angle, tends to reduce the protectiveness of the safety glasses, can cause the safety glasses to fall off of the user's face, is uncomfortable, looks awkward, and makes it difficult to remove either the safety glasses and/or the ear muffs, among countless other disadvantages. It is also undesirable for the user to place the arms of safety glasses under the ear muffs because: this tends to be incredibly uncomfortable as the ear muffs apply pressure on the arms of the safety glasses forcing them into the side of the user's head, can reduce the ear muff's ability to block noise because of spaces caused by the arms of the safety glasses, this makes it difficult and/or painful to move the safety glasses when the ear muffs are pressing inward on the arms of the safety glasses, makes it difficult to remove the safety glasses without removing the ear muffs first, and can prevent a user from placing the safety glasses at their most desired and effective position, among countless other disadvantages.

In view of these deficiencies in the prior art, and for or the reasons stated above, and for other reasons stated below which will become apparent to those skilled in the art upon reading and understanding the specification, claims and drawings, there is a need in the art for an improved ear and eye protection system.

Thus, it is a primary object of the invention to provide an improved ear and eye protection system and method that improves upon the state of the art.

Another object of the invention is to provide an improved ear and eye protection system that is simple in design.

Yet another object of the invention is to provide an improved ear and eye protection system that has a long useful life.

Another object of the invention is to provide an improved ear and eye protection system that is comfortable to use and wear.

Yet another object of the invention is to provide an improved ear and eye protection system that effectively protects both vision and hearing.

Another object of the invention is to provide an improved ear and eye protection system that promotes safety and safe working practices.

Yet another object of the invention is to provide an improved ear and eye protection system that can be used with practically any pair of safety glasses.

Another object of the invention is to provide an improved ear and eye protection system that provides various levels of hearing protection.

Yet another object of the invention is to provide an improved ear and eye protection system that allows a user to adjust the hearing protection level.

Another object of the invention is to provide an improved ear and eye protection system that allows a user to hear without having to remove the ear protection.

Yet another object of the invention is to provide an improved ear and eye protection system that allows safety glasses to be quickly and easily moved into and out of the user's line-of-sight.

Another object of the invention is to provide an improved ear and eye protection system that allows hearing protection and eye protection to be simultaneously worn in a comfortable and effective manner.

Yet another object of the invention is to provide an improved ear and eye protection system that provides doors in the ear muffs that provide for tiered hearing levels.

Another object of the invention is to provide an improved ear and eye protection system that provide slots that receive the arms of safety glasses.

Yet another object of the invention is to provide an improved ear and eye protection system that does not force the arms of safety glasses into contact with the side of a user's head.

Another object of the invention is to provide an improved ear and eye protection system that allows safety glasses to be pivoted upward to rest on a user's forehead.

Yet another object of the invention is to provide an improved ear and eye protection system that will hold safety glasses in any position the user moves the safety glasses to.

Another object of the invention is to provide an improved ear and eye protection system that eliminates or reduces the possibility of losing or misplacing the safety glasses or hearing protection.

Yet another object of the invention is to provide an improved ear and eye protection system that provides a single integrated system.

Another object of the invention is to provide an improved ear and eye protection system that saves time.

Yet another object of the invention is to provide an improved ear and eye protection system that improves safety.

Another object of the invention is to provide an improved ear and eye protection system that is easy to use.

Yet another object of the invention is to provide an improved ear and eye protection system that has a minimum number of parts.

Another object of the invention is to provide an improved ear and eye protection system that is high quality.

Yet another object of the invention is to provide an improved ear and eye protection system that has a minimum number of parts.

These and other objects, features, or advantages of the invention will become apparent from the specification and claims.

SUMMARY OF THE INVENTION

An eye and ear protection system includes a pair of ear muffs connected together by a strap, the ear muffs include a slot in their forward side that is connected to a cavity within the ear muffs. The arms of a pair of glasses are positionable within the slots and allow a user to move the glasses between an in the line-of-sight position and an out of the line-of-sight position. The ear muffs also include one or two doors that can be opened, to allow the user to hear sounds in the environment, and closed to protect the user from loud noises in the environment. This system improves comfort and allows the user to selectively deploy hearing protection and/or eye protection without the need to remove the system from their head which saves time and reduces the potential for losing or misplacing either the hearing or eye protection.

DETAILED DESCRIPTION

Figure 1:
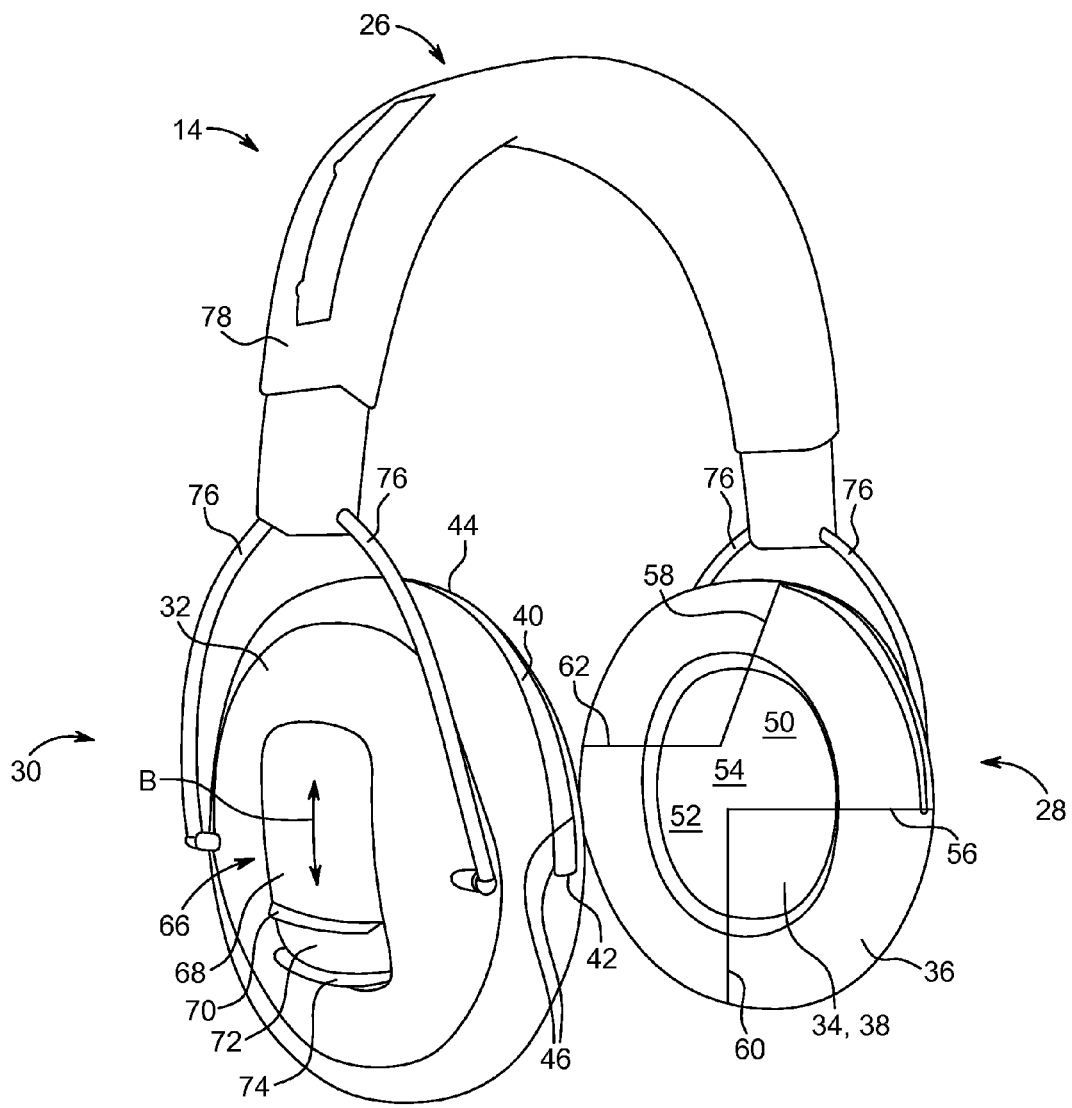
FIG. 1 is a perspective view of an eye and ear protection system, the view showing an ear protection system having a pair of ear muffs connected to one another by a strap, the ear muffs having a slot in the upper forward side of the ear muffs, the view also showing the outline of a cavity positioned within the ear muffs and connected to the slot, the view also showing a pair of doors having tabs which are positioned in the cup of the ear muffs, the view also showing a flexible boot connected to the cup of the ear muffs.
Figure 2:
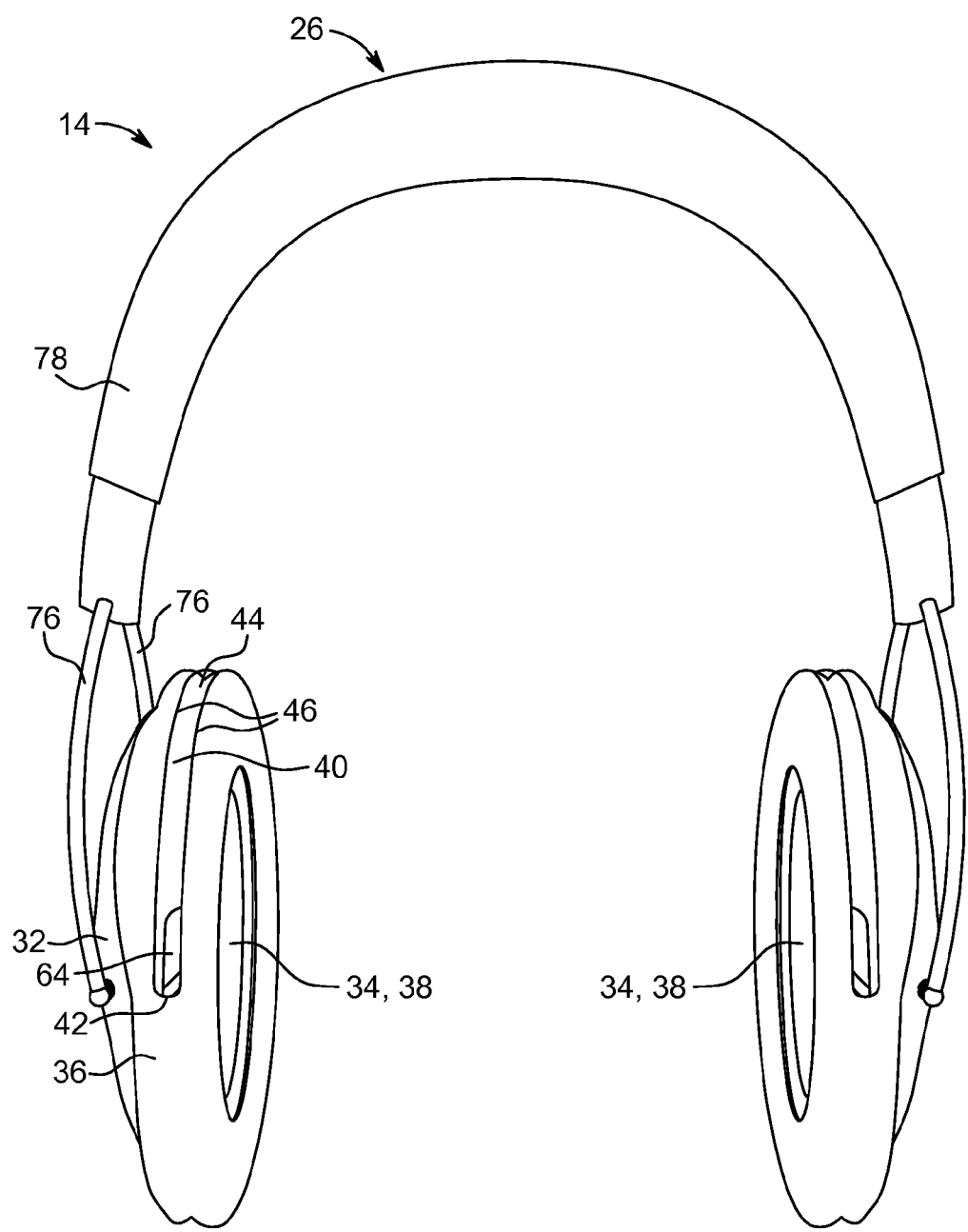
FIG. 2 is a front elevation view of the eye and ear protection system of FIG. 1, the view showing an ear protection system having a pair of ear muffs connected to one another by a strap, the ear muffs having a slot in the upper forward side of the ear muffs, the view also showing a flexible boot connected to the cup of the ear muffs.
Figure 3:
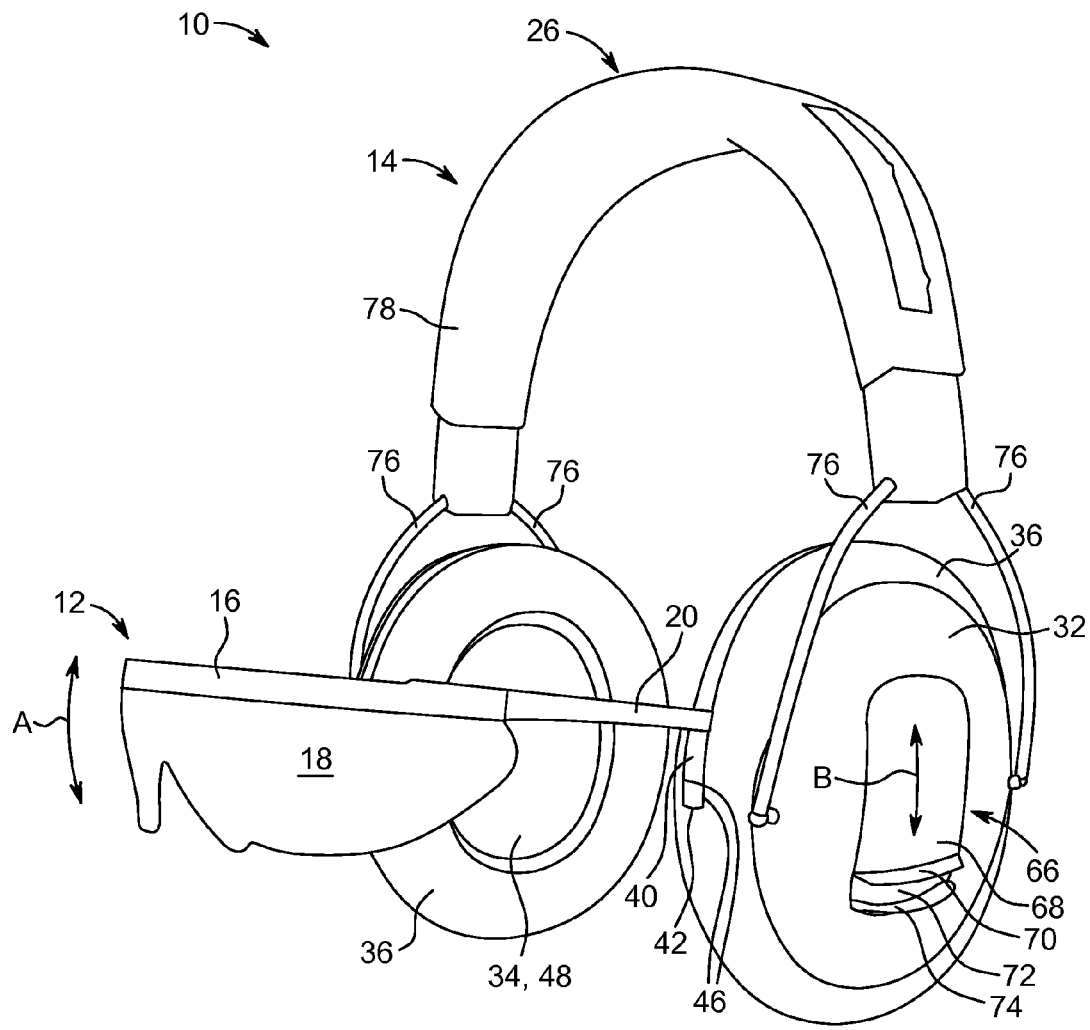
FIG. 3 is a perspective view of the eye and ear protection system of FIG. 1, the view showing an ear protection system having a pair of ear muffs connected to one another by a strap, the ear muffs having a slot in the upper forward side of the ear muffs, the view also showing a pair of doors having tabs which are positioned in the cup of the ear muffs, the view also showing a flexible boot connected to the cup of the ear muffs; the view also showing an eye protection system in the form of a pair of glasses having a frame, lenses and arms connected to the ear protection system by the arms being inserted through the slots and into the cavity of the ear muffs thereby holding the eye protection system in place, the view showing the eye protection system in an in the line-of-sight position.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that mechanical, procedural, and other changes may be made without departing from the spirit and scope of the invention. The following detailed description is, therefore, not to be taken in a limiting sense, and the scope of the invention is defined only by the appended claims, along with the full scope of equivalents to which such claims are entitled.

As used herein, the terminology such as vertical, horizontal, top, bottom, front, back, end, sides, and the like, are referenced according to the views presented and/or the orientation of the parts/components with respect to one another. It should be understood, however, that the terms are used only for purposes of description, and are not intended to be used as limitations. Accordingly, orientation of an object or a combination of objects may change without departing from the scope of the invention.

With reference to the figures, an eye and ear protection system 10 (system 10) is presented. The system 10 includes an eye protection system 12 and an ear protection system 14.

Eye Protection System:

Eye protection system 12 is formed of any suitable size, shape and design and serves to allow a user to see through the eye protection system 12 while simultaneously protecting the user's eyes. In one arrangement, as is shown, eye protection system 12 is a pair of eye glasses or safety glasses. Any form of eye glasses, safety glasses, safety shield, blast shield, sun glasses, prescription glasses, non-prescription glasses, reading glasses, safety goggles, or the like are hereby contemplated for use as eye protection system 12.

In the arrangement shown, eye protection system 12 includes a frame 16, one or more lenses 18 and arms 20. Frame 16 is any form of a frame or support device that holds the components of eye protection system 12 together. Lens or lenses 18 are any form of a device that allows the user to see there through while protecting the user's eyes. Arms 20 are any form of a device that connects to and holds onto the user's head while positioning the lenses 18 in the proper placement.

In the arrangement shown, arms 20 connect adjacent their forward end to the rearward or outside end of frame 16 and/or lenses 18. In one arrangement, as is shown, arms 20 connect to frame 16 by a hinge 22. Hinge 22 allows arms 20 to fold with respect to frame 16 and lenses 18. In a collapsed configuration, or storage position, anus 20 are folded over one another and are positioned in approximate parallel alignment to one another and extend in an approximate parallel alignment to the side-to-side width of frame 16 and lenses 18. In another arrangement, hinges 22 are not present and arms 20 are not collapsible.

Arms 20 are formed of any suitable size, shape and design. In the arrangement shown, when viewed from the side, arms 20 are generally thin and elongated from a forward end to a rearward end. The rearward end of arms 20 of many eye protection systems 12 either extend straight rearward before terminating, or extend rearward before curving downward. In the arrangement wherein arms 20 extend straight, or generally straight rearward before terminating, these arms 20 are intended to engage the side of a user's head and be positioned above the user's ears. In the arrangement wherein arms 20 extend rearward before curving downward, these arms 20 are intended to engage the side of a user's head and be positioned above the user's ears, with the downwardly curving section intended to wrap around, or partially around, and behind the user's ears. This downward curvature or wrap-around section is intended to help the arms 20 hold onto the user's head or ears, especially when the user looks down. In addition, the ends of arms 20 of many eye protection systems 12 extend inward as they extend rearward. This inward extension is intended to help the arms 20 hold onto the user's head, especially when the user looks down.

In an alternative arrangement, when viewed from the side, the arms 20 of many eye protection systems 12 are wide at or near where the arms 20 connect to frame 16, lenses 18, and/or hinges 22 and taper to be narrower at or near where the arms contact the user's head or are positioned above the user's ear. This wide portion of arms 20 at or near fame 16, lenses 18, and/or hinges 22 serves to provide additional protection to the user's eyes by preventing particles, material or objects from entering the user's eyes from the side.

There is an endless array of sizes, shapes and designs of eye protection systems 12 which are all contemplated for use herein and are intended to be usable as part of the eye and ear protection system 10. As such, the variation from conventional eye protection system 12 to eye protection system 12 is intended to be accounted for herein.

Ear Protection System:

Ear protection system 14 is formed of any suitable size, shape and design and serves to both selectively protect the user's hearing while also holding the eye protection system 12 in a user-selected position. In one arrangement, as is shown, ear protection system 14 is formed of a pair of opposing ear muffs 24 connected to one another by a strap 26. Ear protection system 14 has a forward side 28 and a rearward side 30.

Ear muffs 24 are formed of any suitable size, shape and design and serves to fit over a user's ears and selectively block loud noises so as to protect the user's hearing. In the arrangement shown, as one example, each of the pair of opposing ear muffs 24 are formed of a cup 32. Cup 32, when vied from the side is generally circular or oval in shape, which serves to comfortably fit around a user's ear, however any other shape is hereby contemplated for use. In the arrangement shown, cup 32 is arcuate or curved and smoothly slopes from the outward surface to the inward edge, thereby forming a cup or bowl shape having a hollow interior 34.

A boot 36 is connected to the inward edge of cup 32. Boot 36 is formed of any suitable size, shape and design and serves to seal to the side of the user's head around their ear so as to prevent sound from entering the interface between cup 32 and the user's head. In one arrangement, boot 36 is formed of a compressible material, a flexible material or a semi-compressible or semi-flexible material, which both provides user-comfort as well being slightly deformable so as to accommodate differences from user-to-user. Any material is hereby contemplated for use as boot 36, however examples include, foam, rubber, foam rubber, plastic, fabric, or any combination thereof, or the like.

In one arrangement, boot 36 has a hollow center and therefore connects to the inward edge of cup 32, but does not extend across the hollow interior 34 of cup 32. In this arrangement, the material of cup 32 provides much of the hearing protection to the user's ears; or alternatively in this arrangement, an additional layer of sound-absorbing material 38 is positioned within the hollow interior 34 of cup 32 to absorb or prevent sounds from reaching the user's ear. In an alternative arrangement, boot 36 connects to the inward edge of cup 32 as well as extends across the hollow interior 34 of cup 32, and in this way, the layer of sound-absorbing material 38 is connected to or part of boot 36.

Ear muffs 24 include a slot 40. Slots 40 are formed of any suitable size, shape or design and serve to receive and hold the rearward ends of arms 20 of eye protection system 12. In one arrangement, as is shown, when viewed from the forward side 28 of ear muffs 24 slots are generally square or rectangular in shape. In the arrangement shown, when viewed from the forward side 28 of ear muffs 24, slots extend from a bottom end 42, which is positioned at approximately the midpoint, or forward-most point, of the forward side 28 of ear muffs 24, to an upper end 44, which is positioned at approximately the midpoint, or upper-most point, of the upper side of ear muffs 24; however any other placement for bottom end 42 and upper end 44 is hereby contemplated for use. As one example, to accommodate eye protection systems 12 that have especially wide arms 20 (which provide added protection from the side) bottom end 42 is positioned lower and below the midpoint of the forward side 28 of ear muffs 24, and upper end 44 is positioned further rearward than the midpoint of the upper end of ear muffs 24, so as not to inhibit movement of the eye protection system 12 between an in the line-of-sight position and an out of the line-of-sight position. Also, in the arrangement shown, slots 40 include approximately flat or straight sidewalls 46 that extend in approximate parallel spaced alignment to one another and extend between upper end 44 and bottom end 42, giving slot 40 a generally constant width.

Slots 40 are connected to a cavity 48. Cavity 48 is formed of any suitable size, shape and design, and serves to receive and hold the rearward ends of arms 20 therein while allowing user selected movement of the eye protection system 12 between an in the line-of-sight position and an out of the line-of-sight position. In one arrangement, cavity 48 has a generally constant width or thickness, whereas in an alternative arrangement, cavity 48 varies in width or thickness across its vertical or lateral length. In one arrangement, cavity 48 is generally flat and straight from forward side 28 to rearward side 30, whereas in an alternative arrangement, cavity 48 curves as it extends from forward side 28 to rearward side 30.

In one arrangement, as is shown, cavity 48 extends from the forward side 28 of ear muff 24 to the rearward side 30 of ear muff 24, with the forward side of cavity 48 connecting to slot 40. In one arrangement, cavity 48 is formed of a forward section 50 and a rearward section 52 that are connected to one another at a midsection 54. In the arrangement shown, forward section 50 is generally triangular in shape and connects at its forward edge to slot 40 and extends rearward and connects at its rearward end to midsection 54. As forward section 50 extends rearward it narrows. Similarly, rearward section 52 is generally triangular in shape and extends forward from the inside surface of cup 32 and connects at its forward end to midsection 54. As rearward section 52 extends forward it narrows. In this arrangement, forward section 50 and rearward section 52 like a pair of oppositely facing triangles that are positioned in overlapping condition, with the overlapping portion being the midsection 54.

In this arrangement, the forward section 50 is defined by a bottom wall 56 and an upper wall 58. The forward end of the bottom wall 56 connects to the bottom end 42 of slot 40, and the forward end of the upper wall 58 connects to the upper end 44 of slot 40. Similarly, the rearward section 52 is defined by a bottom wall 60 and an upper wall 62. The rearward end of the bottom wall 60 terminates at its rearward end at or before the inward surface of cup 32, and the rearward end of the upper wall 62 terminates at its rearward end at or before the inward surface of cup 32. The bottom wall 56 and upper wall 58 and bottom wall 60 and upper wall 62 converge toward one another or narrow as they extend inward toward one another before bottom walls 56, 60 and upper walls 58, 62 connect to one another at midsection 54. In this way, midsection 54 forms a pivot point where the arms 20 of eye protection system 12 pivot when eye protection system 12 is moved between in in the line-of-sight position and an out of line-of-sight position, or any position in-between. These upper walls 58, 62 and bottom walls 56, 60 can be placed at any position to accommodate various eye protection systems 12.

Figure 4:
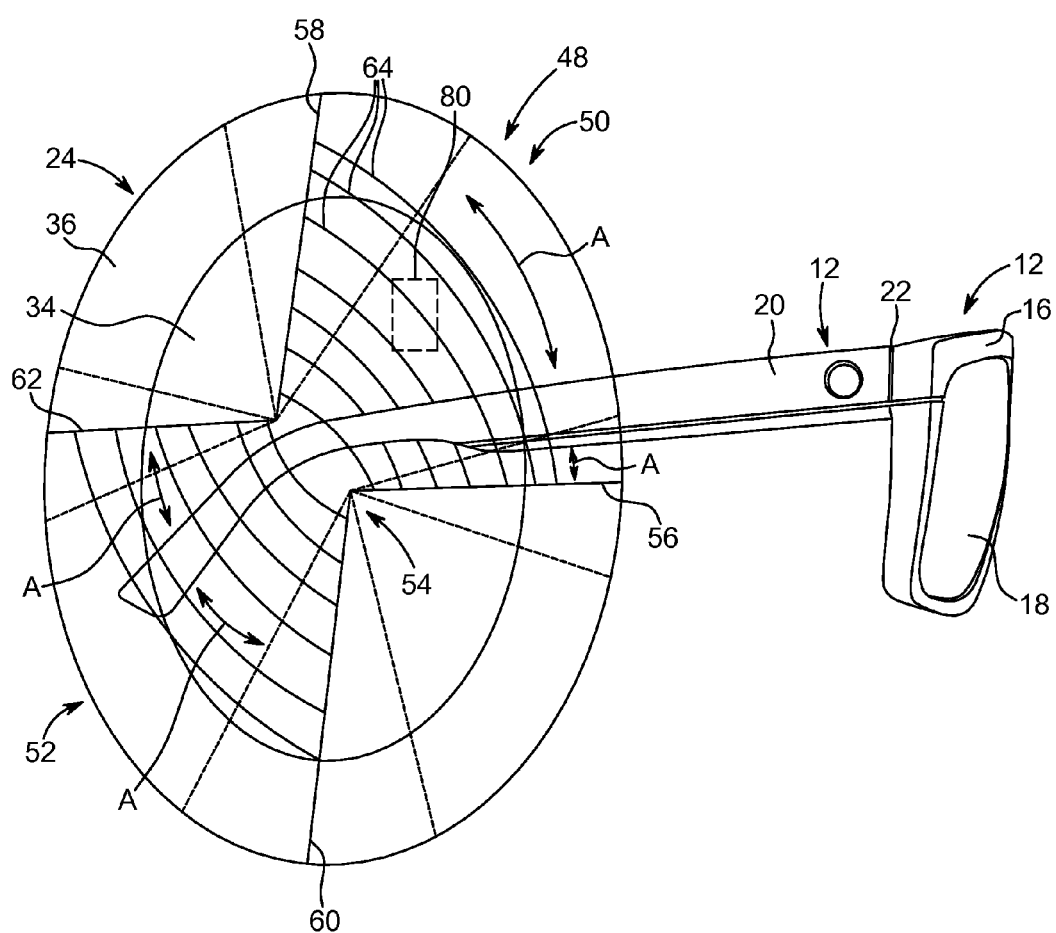
FIG. 4 is a side cut-away elevation view of the eye and ear protection system of FIG. 1, the view showing an ear muff having a slot in the upper forward side of the ear muff, the view showing the shape of the cavity within the ear muff, including the triangular forward section and rearward section which are positioned in overlapping condition at the midsection, the view showing arcuate friction members in the cavity, the view also showing an eye protection system positioned within the cavity, the view also showing alternative sizes and shapes for the cavity in dashed lines.

In the arrangement shown in FIG. 4, the dashed lines depict alternative positions for upper walls 58, 62 an bottom walls 56, 60 that make cavity 48, and forward section 52 and rearward section 52 either wider or narrower, or have a higher or lower termination point.

Also shown in FIG. 4 is an eye protection system 12 with arms 20 positioned within cavity 48. As can be seen from this view, the arms 20 curve downward toward their rearward end, which is held in rearward section 52 while the generally straight portion of arms 20 is held within the forward section 50. Arrows A depict the angle or arc of curvature of arms 20 when moving between an in the line-of-sight position and an out of the line-of-sight position. Arms 20 generally pivot at midsection 54 when being moved between an in the line-of-sight position and an out of the line-of-sight position. This view shows the reason for having a forward section 50 and rearward section 52, as the rearward section 52 is needed to accommodate the downwardly curving rearward portions of arms 20 when moving the eye protection system between an in the line-of-sight position and an out of the line-of-sight position. However, in an alternative arrangement, no rearward section 52 and forward section 50 is present and cavity extends all, a majority of, or a portion of the hollow interior 34 without being bifurcated into two generally triangular sections.

Cavity 48 includes a fiction member 64 positioned therein. Friction member 64 is formed of any suitable size, shape and design and serves to apply friction to the arms 20 of eye protection system 12 when arms 20 are positioned within cavity 48 so as to hold eye protection system 12 in any user selected position. In one arrangement, friction member 64 is formed of a plurality of flexible arms (such as rubber, plastic, felt, fabric, composite or the like) that deflect to allow arms 20 to be inserted within cavity 48 and removed from cavity 48 while applying enough pressure or friction to hold the eye protection system 12 in any user selected position while still allowing the position of the eye protection system 12 to be easily adjusted by the user. In one arrangement, friction member 64 is positioned in all or a portion of the forward section 50, the rearward section 52 and/or the midsection 54. Alternatively, friction member 52 is a layer of compressible material or high-friction material, such as a layer of plastic, rubber, fabric, composite or like that prevents eye protection system 12 from unintentionally moving. In the arrangement shown in FIG. 4, friction member 64 is a plurality of flexible arms that are aligned in an arc along the direction of tilting of arms 20 when the eye protection system is move between an in the line-of-sight position and an out of the line-of-sight position. Alternatively, cavity 48 is formed of friction member 52. Any other manner, method or means of preventing eye protection system 12 from unintentionally moving within cavity 48 is hereby contemplated for use.

One or both ear muffs 24 include one or more doors 66. Doors 66 are formed of any suitable size, shape and design and serve to be opened, to allow a user to hear sounds in the environment without having to remove the ear muffs 24, and closed to seal off sounds in the environment from reaching the user's ears. In one arrangement, as is shown, a first door 68 having a first tab 70 and a second door 72 having a second tab 74 are positioned in each ear muff 24. The pair of doors 68, 72 slide vertically along arrow B within cups 32 of ear muffs 24, the further the doors 68, 72 slide upward, the more sounds from the environment can enter the ear muffs 24. When both doors 68, 72 are fully closed, this provides the greatest amount of hearing protection. In this way, the doors 68, 72 provide tiered hearing, meaning that when the first door 68 is opened it provides an improved ability to hear sounds in the environment as opposed to when the first door 68 is closed, and when the first door 68 and second door 72 are opened it provides an improved ability to hear sounds in the environment as opposed to when only the first door 68 is opened. A user can select to only open the first door 68 by grasping the first tab 70 and sliding it vertically to any position between fully open and fully closed. Similarly, the user can select to open both first door 68 and second door 72 simultaneously by grasping second tab 74 and sliding it vertically upward, which opens both the first door 68 and the second door 72. When both doors 68, 72 are open, a user can select to only close the second door 72 by grasping the second tab 74 and sliding it vertically to any position between fully open and fully closed. Similarly, the user can select to close both first door 68 and second door 72 simultaneously by grasping first tab 70 and sliding it vertically downward, which closes both the first door 68 and the second door 72.

In one arrangement, tabs 70, 74 are brightly colored, such as yellow, orange, red, white, blue, green or the like or a neon color, as compared to the coloring of the rest of ear protection system 14 and/or ear muffs 24. This bright coloring makes it easier for others to see the position of doors 68, 72 and therefore determine whether the user can hear noises in the environment. This ability to quickly and easily spot whether the user has deployed the doors 68, 72 and therefore has sealed of noises in the environment, is a safety feature, and prevents others from assuming that the user can hear them.

Strap 26 is formed of any suitable size, shape and design and serves to connect opposing ear muffs 24 together. In one arrangement, as is shown, strap 26 arcuately connects opposing ear muffs 24 and includes a pair of spokes 76 that connect to opposing sides of ear muffs 24 and allow ear muffs 24 to tilt thereon to accommodate a user's head. Strap 26 also includes a padding member 78 that provides additional user comfort.

In one arrangement, ear protection system 14 includes an electronic device 80 that serves to provide communication as well as entertainment to services to the user. As one example, electronic device is a Bluetooth device that allows for both wireless communication (such as cell phone communication) and/or entertainment services such as listening to music. In one arrangement, electronic device 80 includes a microphone, for receiving sounds, and a speaker for transmitting sounds, as well as a wireless communication mechanism and a power source, such as a battery. Incorporating electronic device 80 within ear protection system 14 eliminates the need for the user to remove the hearing protection when they want to listen to music or make a phone call, thereby further encouraging use of the hearing protection.

In Operation:

User places ear protection system 14 on their head with strap 26 arching over their head and ear muffs 24 placed around their ears. When in place, boot 36 of each ear muff 24 seals against the user's head thereby preventing undesired noises from entering hollow interior 34 of ear muffs 24.

Next, the user inserts the rearward ends of arms 20 of eye protection system 12 into the slots 40. As the arms 20 are inserted through slots 40, the arms 20 enter cavity 48. In the arrangement, where friction member 64 is positioned within cavity 48, friction member 64 deflects to allow arms 20 to pass while applying enough friction or resistance to hold the arms 20 in place once the user has adjusted eye protection system 12 appropriately. Once the user lets go of the eye protection system 12, the friction member 64 holds the eye protection system 12 in the user selected position.

To move the eye protection system 12 into an out of the line-of-sight position, the user simply grasps the eye protection system 12 and slides it up within cavity 48. This causes the arms 20 to overcome the holding friction of engagement with the cavity 48 and/or engagement with the friction member 64. As the eye protection system 12 is moved upward, the arms 20 pivot at approximately the midsection 54 of cavity 48. Once the eye protection system 12 is in the out of the line-of-sight position, the eye protection system 12 is automatically held in place. This allows s user to see without the obstruction of the eye protection system 12, and eliminates the need to remove the eye protection system 12 altogether.

To move the eye protection system 12 into an in the of the line-of-sight position, the user simply grasps the eye protection system 12 and slides it down within cavity 48. This causes the arms 20 to overcome the holding friction of engagement with the cavity 48 and/or engagement with the friction member 64. As the eye protection system 12 is moved downward, the arms 20 pivot at approximately the midsection 54 of cavity 48. Once the eye protection system 12 is in the in the line-of-sight position, the eye protection system 12 is automatically held in place. This allows a user to quickly and easily deploy the eye protection system 12 without pain or without having to remove the ear protection system 14.

If the user desires to hear sounds in the environment, the user simply grasps one or both of the tabs 70, 74 and slides one or both of the doors 68, 72 upward until the desired level of hearing is obtained. If the user desires to block sounds in the environment, the user simply grasps one or both of the tabs 70, 74 and slides one or both of the doors 68, 72 downward until the desired level of hearing is obtained.

Figure 5:
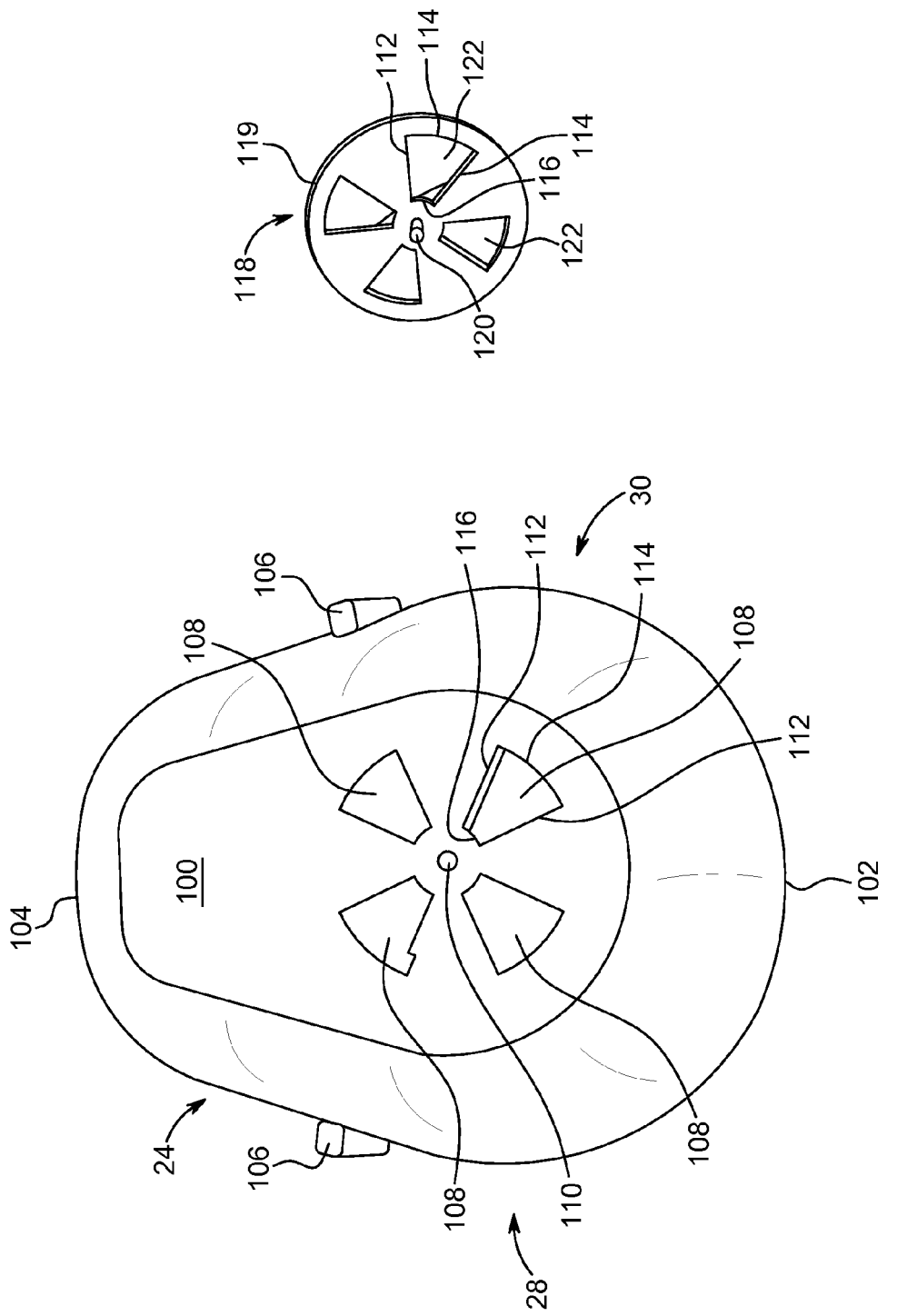
FIG. 5 is an exploded perspective view of an alternative arrangement of an ear muff having a flat planar surface and a plurality of openings therein, the view also shows a cover that is configured to be rotatably attached over the openings, the cover itself includes a plurality of openings.
Figure 6:
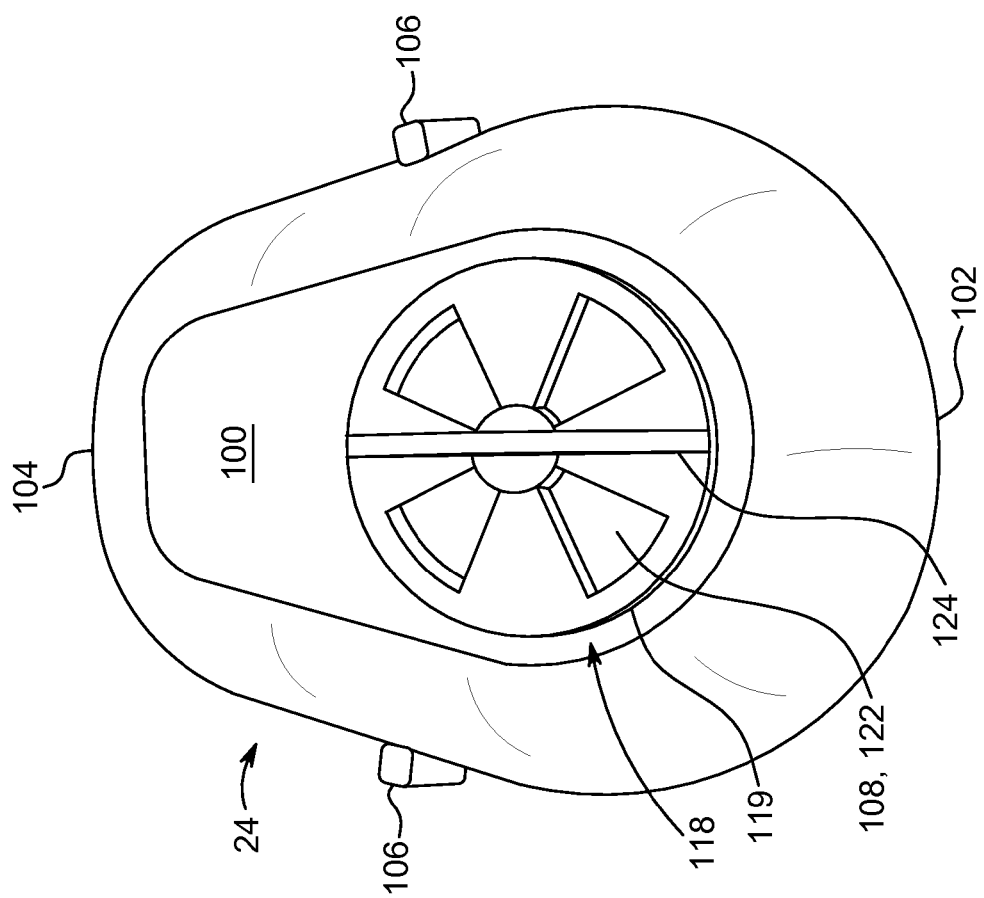
FIG. 6 is an assembled perspective view of the alternative arrangement shown in FIG. 5, the view showing the cover rotated to an open position.
Figure 7:
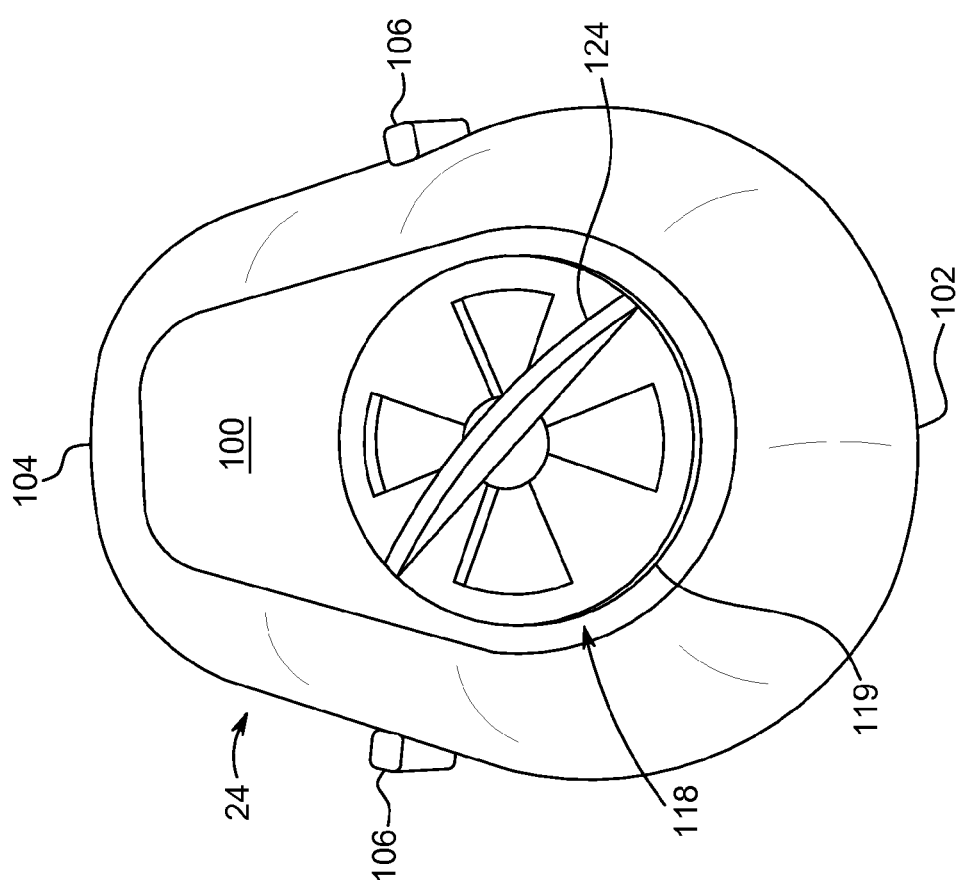
FIG. 7 is an assembled perspective view of the alternative arrangement shown in FIGS. 5 and 6, the view showing the cover rotated to a closed position.

Alternative Arrangement of Ear Muffs:

With reference to FIGS. 5-7 an alternative arrangement for ear muffs 24 is presented. In this arrangement, ear muffs 24 have a generally flat planar surface 100 positioned at their outward side and slope in generally rounded fashion inward toward the user's head there from. In this way, ear muff 24 forms the hollow interior 34 in which the user's ear fits. In one arrangement, as is shown, when viewed from the side, ear muff 24 is a rounded somewhat oval shape that is vertically elongated with the bottom end 102 of the rounded shape being slightly larger than the upper end 104 of the rounded shape. In this way, when viewed from the side, ear muff 24 is formed in a teardrop shape with a rounded upper end instead of a pointed upper end.

Ear muffs 24 includes a pair of sockets 106, one positioned in the forward side 28 and one positioned in the rearward side 30 of ear muffs 24. In this way, sockets 106 are positioned on opposite sides of ear muff 24 from one another at or near the midsection of ear muff 24 between bottom end 102 and upper end 104. The inward ends of spokes 76 connect to sockets 106 and allow ear muffs 24 to pivot thereon to allow ear muffs 24 to comfortably fit any user.

Planar surface 100 includes a plurality of openings 108 therein that serve to allow sound to pass there through to be heard by the user. In the arrangement shown, openings 108 are centered on a centrally positioned axis 110, which is itself an opening as well. In the arrangement shown, four openings 108 are positioned at equal spacing around the centrally positioned axis 110 which is circular in shape. In this arrangement, openings 108 have a pair of opposing flat sidewalls 112 that angle inward toward one another as they extend from exterior wall 114 to interior wall 116. The planes established by sidewalls 112 point at, or extend outward from, the axis 110, and/or the axis of rotation. In this arrangement, exterior wall 114 is rounded or is formed of a partial circle which is centered on axis 110. Similarly, the interior wall 116 is also rounded or is formed of a partial circle which is centered on axis 110. When both exterior wall 114 and interior wall 116 are formed of a partial circle which is centered around axis 110, this causes the exterior wall 114 to be concave in shape and the interior wall 116 to be convex in shape.

With four openings 108, each opening occupies approximately 45° of a circle. That is, the four openings 108 are spaced apart from one another by 45° and the openings 108 take up approximately 45° of a circle. The interior wall 116 of openings 108 is spaced a distance outward from the exterior wall of axis 110.

A cover 118 is formed of any suitable size, shape and design and serves to selectively cover and uncover openings 108. In one arrangement, as is shown, cover 118 is generally planar in shape, when viewed from one side. Cover 118 includes and circular in shape when viewed from another side, which is bounded by a circular outside wall 119. Cover 118 includes an axle 120 positioned at its approximate center. Axle 122 extends inward from an inward side of cover 118 and is configured to be rotatably received within axis 110.

Like planar surface 100, cover 118 includes four openings 122 therein that serve to allow sound to pass there through to be heard by the user when the openings 122 in cover 118 are aligned with the openings 108 in flat planar surface 100. In the arrangement shown, openings 122 are centered on axle 120, which is itself circular. In the arrangement shown, four openings 1122 are positioned at equal spacing around the centrally positioned axle 120; however any other number of openings is hereby contemplated for use such as one, two, three, five, six, seven, eight or more. In this arrangement, openings 122, like openings 108, have a pair of opposing flat sidewalls 112 that angle inward toward one another as they extend from exterior wall 114 to interior wall 116. The planes established by sidewalls 112 point at, or extend outward from, the axle 120, and/or the axis of rotation. In this arrangement, exterior wall 114 is rounded or is formed of a partial circle which is centered on axle 120, and/or the axis of rotation. Similarly, the interior wall 116 is also rounded or is formed of a partial circle which is centered on axle 120, and/or the axis of rotation. When both exterior wall 114 and interior wall 116 are formed of a partial circle which is centered around axle 120, and/or the axis of rotation, this causes the exterior wall 114 to be concave in shape and the interior wall 116 to be convex in shape.

With four openings 122, each opening occupies approximately 45° of a circle. That is, the four openings 122 are spaced apart from one another by 45° and the openings 122 take up approximately 45° of a circle. With that said, in one arrangement, the openings of cover 118 are slightly smaller than the openings 108 of flat planar surface 100 such that the material between openings 122 of cover 118 is large enough to cover the openings 108 in flat planar surface when cover is rotated to a closed position.

The interior wall 116 of openings 108 is spaced a distance outward from the exterior wall of axle 120, and/or the axis of rotation.

The exterior surface of cover 118, opposite the side where axle 120 extends from, includes a grip member 124. Grip member 124 is any device which a user can grasp to operate cover 118. In the arrangement shown, grip member 124 is a flange that extends outward from the exterior surface of cover 118 and extends from outside wall 119 to outside wall 119 across the center of cover 118.

In one arrangement, ear muff 24 is formed of a dual durometer arrangement, wherein the exterior of ear muff 24, such as the flat planar surface 100, is formed of a generally hard and rigid material, whereas the interior side, or the side that contacts the user's head, is formed of a soft and flexible material. In an alternative arrangement, a boot 36, as is described herein, covers the interior side, or side of ear muff 24 that contacts the user's head.

In operation, the arrangement shown in FIGS. 5-7, the cover 118 is installed on the flat planar surface 100 by inserting axle 120 in the axis 110 which rotatably receives axle 120 therein with tight and close tolerances. Once inserted, cover 118 can be rotated upon axle 120, but cover 118 cannot be removed. To accomplish this, any arrangement is used such as a snap-fit feature, a groove and tongue arrangement, a clasp, a hook and barb arrangement, a pressure fit arrangement, a compressible bulb on axle 120, or the like or any other similar arrangement. Once cover 118 is installed on flat planar surface 100, cover 118 is in frictional engagement with ear muff 24. This frictional engagement allows the user to rotate cover 118 on axis 110 and axle 120 by applying a force greater than the resistance caused by the frictional engagement. This friction holds the cover 118 in the user set position and prevents the cover 118 from unintentionally rotating.

When the user desires the maximum ability to hear sounds in the environment without removing system 10, the user grasps grip member 124 and rotates cover 118 until the openings 122 in cover 118 fully align with the openings 108 in flat planar surface 100. This arrangement, which is shown in FIG. 6, allows the greatest amount of sound to pass to the user's ear.

When the user desires maximum hearing protection the user grasps grip member 124 and rotates cover 118 until the openings 122 in cover 118 fully offset with the openings 108 in flat planar surface 100. This arrangement, which is shown in FIG. 7, allows the greatest amount of sound to be blocked from the user's ear.

From the above discussion and the accompanying drawings and claims it will be appreciated that the improved eye and ear protection system presented offers many advantages over the prior art. That is, the improved eye and ear protection system presented: is simple in design; has a long useful life; is comfortable to use and wear; effectively protects both vision and hearing; promotes safety and safe working practices; can be used with practically any pair of safety glasses; provides various levels of hearing protection; allows a user to adjust the hearing protection level; allows a user to hear without having to remove the ear protection; allows safety glasses to be quickly and easily moved into and out of the user's line-of-sight; allows hearing protection and eye protection to be simultaneously worn in a comfortable and effective manner; provides doors in the ear muffs that provide for tiered hearing; provide slots that receive the arms of safety glasses; does not force the arms of safety glasses into contact with the side of a user's head; allows safety glasses to be pivoted upward to rest on a user's forehead; will hold safety glasses in any position the user moves the safety glasses to; eliminates or reduces the possibility of losing or misplacing safety glasses or hearing protection; provides a single integrated system; saves time; improves safety; is easy to use; has a minimum number of parts; and is high quality, among countless other improvements and advantages.

It will be appreciated by those skilled in the art that other various modifications could be made to the device without parting from the spirit and scope of this invention. All such modifications and changes fall within the scope of the claims and are intended to be covered thereby. It should be understood that the examples and embodiments described herein are for illustrative purposes only and that various modifications or changes in light thereof will be suggested to persons skilled in the art and are to be included within the spirit and purview of this application.

What is claimed:

1. An improved eye and ear protection system, comprising:
   a hearing protection system, comprising:
      a pair of opposing ear muffs;
      the pair of ear muffs connected together by a strap;
      the pair of ear muffs having a forward side and a rearward side, and an upper side and a lower side;
      the pair of ear muffs having an outside layer;
      the pair of ear muffs having an inside layer;

the pair of ear muffs having a cavity positioned between the outside layer and the inside layer;

the cavity in the pair of ear muffs having a forward side and a rearward side, and an upper side and a lower side;

the cavity in the pair of ear muffs extending a vertical height;

the cavity in the pair of ear muffs extending a lateral width;

the cavity in the pair of ear muffs having a forward section, a rearward section and a middle section;

wherein the forward section of the cavity is positioned adjacent the forward side of the pair of ear muffs, the rearward section of the cavity is position adjacent the rearward side of the pair of ear muffs and the middle section of the cavity is positioned between the forward section and the rearward section;

wherein the middle section of the cavity is narrower than the forward section and rearward section;

a slot positioned in the forward side of the pair of ear muffs, wherein the slot connects to the cavity and provides access into the cavity;

an eye protection system, comprising:

a frame;

lenses connected to the frame;

arms connected to the frame; and wherein the arms of the eye protection system are removably positioned within the cavity of the pair of ear muffs;

wherein when the arms of the eye protection system are positioned within the cavity of the pair of ear muffs, the arms are rotatable between an in the line-of-sight position and an out of the line-of-sight position without removing the arms of the eye protection system from the cavity, of the pair of ear muffs.

2. The system of claim 1, wherein when the eye protection system is the line-of-sight position the arms of the eye protection system are positioned adjacent a lower end of the slot in the pair of ear muffs.

3. The system of claim 1, further comprising:

a first door positioned in one or both of the ear muffs; and wherein when the first door is opened this provides an improved ability to hear sounds in the environment as opposed to when the first door is closed.

4. The system of claim 1, further comprising:

a first door positioned in one or both of the ear muffs;

a second door positioned in one or both of the ear muffs;

wherein the first door is opened this provides an improved ability to hear sounds in the environment as opposed to when the first door is closed; and wherein when the first door and second door are opened this provides an improved ability to hear sounds in the environment as opposed to when only the first door is opened.

5. The system of claim 1, further comprising a wirelessly enabled speaker and microphone associated with the hearing protection system used for communication purposes.

6. The system of claim 1, further comprising a Bluetooth enabled device associated with the hearing protection system and positioned on or in one or both of the ear muffs.

7. The system of claim 1, wherein when viewed from the side, the middle section is narrower, than the forward section and the rearward section.

8. The system of claim 1, further comprising:

a friction imparting member positioned within the cavity; and wherein the friction imparting member serves to hold the arms of the eye protection system in a user selected position.

9. The system of claim 1, further comprising:

at least one opening in one or both of the ear muffs;

a cover rotatably connected to the ear muff;

the cover having at least one opening that selectively covers the at least one opening in the ear muff.

10. The system of claim 1, wherein the arms of the eye protection system rotate within the cavity upon an axis of rotation that extends across the lateral width of the pair of ear muffs.

11. The system of claim 1, wherein the outside layer of the pair of ear muffs is formed of a cup.

12. The system of claim 1, wherein the inside layer of the pair of ear muffs is formed of a boot.

13. The system of claim 1, wherein when the eye protection system is in the out of the line-of-sight position the arms of the eye protection system are positioned adjacent an upper end of the slot of the pair of ear muffs.

14. An improved eye and ear protection system, comprising:

a pair of opposing ear muffs;

the pair of ear muffs connected together by a strap;

the pair of ear muffs having a forward side and a rearward side, and an upper side and a lower side;

the pair of ear muffs having an outside layer;

the pair of ear muffs having an inside layer;

the pair of ear muffs having a cavity positioned between the outside layer and the inside layer;

the cavity in the pair of ear muffs having a forward side and a rearward side, and an upper side and a lower side;

the cavity in the pair of ear muffs extending a vertical height;

the cavity in the pair of ear muffs extending a lateral width;

the cavity in the pair of ear muffs having a forward section, a rearward section and a middle section;

wherein the forward section of the cavity is positioned adjacent the forward side of the pair of ear muffs, the rearward section of the cavity is position adjacent the rearward side of the pair of ear muffs and the middle section of the cavity is positioned between the forward section and the rearward section;

wherein the middle section of the cavity is narrower than the forward section and rearward section;

a slot positioned in the forward side of the pair of ear muffs, wherein the slot connects to the cavity and provides access into the cavity;

wherein arms of an eye protection system are received within the cavity of the pair of ear muffs; and wherein the eye protection system is movable between an in the line-of-sight position and an out of the line-of-sight position while the arms of the eye protection system are held within the cavity of the pair of ear muffs.

15. The system of claim 14, further comprising:

a first door positioned in one or both of the ear muffs; and wherein when the first door is opened it provides an improved ability to hear sounds in the environment as opposed to when the first door is closed.

16. The system of claim 14, further comprising a first door and a second door positioned in one or both of the ear muffs.

17. The system of claim 14, wherein when the eye protection system is in the in the line-of-sight position the arms of the eye protection system are positioned adjacent a lower end of the slot in the pair of ear muffs, and wherein when the eye protection system is in the out of the line-of-sight position the arms of the eye protection system are positioned adjacent an upper end of the slot of the pair of ear muffs.

18. The system of claim 14, further comprising:
at least one opening in one or both of the ear muffs;
a cover rotatably connected to the ear muff;
the cover having at least one opening that selectively covers the at least one opening in the ear muff.

19. An improved eye and ear protection system, comprising:
a hearing protection system, comprising:
a pair of opposing ear muffs;
the pair of ear muffs connected together by a strap;
the pair of ear muffs having a forward side and a rearward side, and an upper side and a lower side;
the pair of ear muffs having an outside layer;
the pair of ear muffs having an inside layer;
the pair of ear muffs having a cavity positioned between the outside layer and the inside layer;
the cavity in the pair of ear muffs having a forward side and a rearward side, and an upper side and a lower side;
the cavity in the pair of ear muffs extending a vertical height;
the cavity in the pair of ear muffs extending a lateral width;
the cavity in the pair of ear muffs having a forward section, a rearward section and a middle section;
wherein the cavity in the pair of ear muffs narrows at the middle section;
a slot positioned in the forward side of the pair of ear muffs, wherein the slot connects to the cavity and provides access into the cavity;
an eye protection system, comprising:
a frame;
lenses connected to the frame;
arms connected to the frame; and
wherein the arms of the eye protection system are removably positioned within the cavity of the pair of ear muffs;
wherein when the arms of the eye protection system are positioned within the cavity of the pair of ear muffs, the arms are rotatable between an in the line-of-sight position and an out of the line-of-sight position without removing the arms of the eye protection system from the cavity of the pair of ear muffs.

20. The system of claim 19, wherein when the eye protection system is in the in the line-of-sight position the arms of the eye protection system are positioned adjacent a lower end of the slot in the pair of ear muffs, and wherein when the eye protection system is in the out of the line-of-sight position the arms of the eye protection system are positioned adjacent an upper end of the slot of the pair of ear muffs.

* * * * *